United States Patent [19]
Haridas et al.

[11] Patent Number: 6,057,303
[45] Date of Patent: May 2, 2000

[54] HIGHLY LIPOPHILIC CAMPTOTHECIN DERIVATIVES

[75] Inventors: Kochat Haridas, San Antonio; Frederick H. Hausheer, Boerne, both of Tex.

[73] Assignee: BioNumerik Pharmaceuticals, Inc., San Antonio, Tex.

[21] Appl. No.: 09/175,508

[22] Filed: Oct. 20, 1998

[51] Int. Cl.$^7$ .................. A61K 31/4745; C07D 491/22; A61P 35/00

[52] U.S. Cl. ................. 514/63; 546/48; 546/14; 514/283

[58] Field of Search ......... 514/283, 63; 546/48, 546/14

[56] References Cited

U.S. PATENT DOCUMENTS

| | | | |
|---|---|---|---|
| 4,446,322 | 5/1984 | Stein | 544/138 |
| 4,820,815 | 4/1989 | Miller | 540/200 |
| 5,726,181 | 3/1998 | Hausheer | 514/283 |
| 5,731,316 | 3/1998 | Cao | 514/283 |

FOREIGN PATENT DOCUMENTS

| | | |
|---|---|---|
| 98/07727 | 2/1998 | WIPO . |
| 98/35940 | 8/1998 | WIPO . |

OTHER PUBLICATIONS

Bundgaard H. Design of Prodrugs. Elsevier. Amsterdam–New York–Oxford. pp. 1–3, 1985.

Greene TW and Wuts PGM. Protective Groups in Organic Synthesis. Second Edition. John Wiley & Sons, Inc. New York./Chichester/Brisbane/Toronto/Singapore. pp. 12, 13, 1991.

*Primary Examiner*—Evelyn Mei Huang
*Attorney, Agent, or Firm*—Thomas J. Dodd

[57] ABSTRACT

Derivatives of Camptothecin are disclosed, particularly derivatives having multiple substitutions at the 'A', 'B' and 'E' rings thereof. The novel compounds are useful in treating a wide variety of susceptible tumors and are potent inhibitors of Topoisomerase I.

10 Claims, No Drawings

HIGHLY LIPOPHILIC CAMPTOTHECIN DERIVATIVES

FIELD OF THE INVENTION

This invention relates to novel and useful derivatives of Camptothecin. The derivatives of this invention include 'A' and 'B' ring multiple substitutions, and a substitution at the C20 position on the 'E' ring. The invention also includes pharmaceutical formulations of the new derivatives, methods of treating various cancers and leukemias by administering an effective amount of the derivatives to a patient, and processes for synthesizing the derivatives from naturally occurring Camptothecin.

BACKGROUND OF THE INVENTION

Camptothecin is a well-known naturally occurring compound which was discovered to possess antineoplastic properties by Wall and Wani in the early 1960s. Efforts have been made since then to improve upon the anti-proliferative properties of Camptothecin and its analogues, and to reduce the unwanted toxicities of this series of agents.

Camptothecin and many of its analogues are very poorly soluble in water. Many such analogues exhibit water solubility of less than five micrograms per milliliter. This poor water solubility originally presented problems of administration of the intended drug, and early efforts were devoted to making the drug practical for administration to human patients.

These early efforts involved the formulation of Camptothecin analogues with sodium hydroxide, in which the compounds were readily soluble. Unfortunately, these formulations caused the opening of the lactone 'E' ring of the analogue, which resulted in both reduced antineoplastic activity and higher unwanted toxicity upon administration.

Another avenue of exploration has been the development of Camptothecin analogues, which exhibited improved water solubility. Compounds which have resulted from this research include the FDA approved drugs Irinotecan (Camptosar®, CPT-11) and Topotecan (Hycamptin®), as well as other analogues in clinical trials and under development.

Improving the water solubility of Camptothecin analogues improves the ease of administration of the drug to patients. However, especially in the case of Irinotecan, the compound is administered is a pro-drug which requires activation in vivo to the hydrophobic active species (SN38). And none of the water soluble analogues developed thus far has dealt with the problem of unwanted toxicity, thought to be mediated in part by the in vivo glucuronidation of the Camptothecin scaffold. Also, these water soluble derivatives are rapidly converted from the active 'E' ring lactone form to the inactive and toxic carboxylate form in plasma.

The inventors of the present application have directed recent efforts in discovering and developing analogues of Camptothecin which are poorly water soluble. Several of these analogues are disclosed in U.S. patent application Ser. Nos. 08/914,207, filed Aug. 17, 1997, and 09/022,310, filed Feb. 11, 1998.

Poorly water soluble Camptothecin analogues are formulated for administration with suitable solvents such as those disclosed in U.S. Pat. Nos. 5,726,181; 5,447,936; 5,468,754; and others referred to in the Information Disclosure Sheet which accompanies this application. Preferred solvents for these poorly water soluble Camptothecin analogues include dimethylacetamide (DMA), dimethylisosorbide (DMI) and N-methylpyrrolidinone (NMP).

The poorly water soluble Camptothecin analogues generally provide increased lactone stability and greater antitumor activity than the water soluble analogues. Some analogues also provide decreased potential for glucuronidation, which is the form most frequently associated with the unwanted toxicities of Camptothecin analogues.

In recent years it has been recognized that a common problem with many of the camptothecin analogues in clinical use is the low physiologic concentration of the drug in the active lactone form. It is well established that the lactone E-ring is correlated with antitumor activity and the open ring carboxylate form is correlated with both unwanted toxicity and a loss of antitumor activity.

When compared to the water soluble camptothecins, the reported concentrations of the lactone species are substantially higher (in mice) for SN38, 9-amino camptothecin, 9-nitro camptothecin and camptothecin. The low levels of lactone species in human plasma are thought to have a major effect in reducing the antitumor activity of camptothecins containing the commonly recognized 20(S) lactone E-ring moiety. It is reasonable to consider that if it were possible to increase the plasma concentration of the lactone species that the maintenance of higher concentrations of the lactone species of a camptothecin would generally result in a relative increase in the antitumor activity of the camptothecins in humans. This invention addresses this key concept and additionally enhances tissue penetration and bioavailability by increasing or maintaining lipophilic nature of the camptothecin molecule.

Structures of Water Soluble Camptothecins

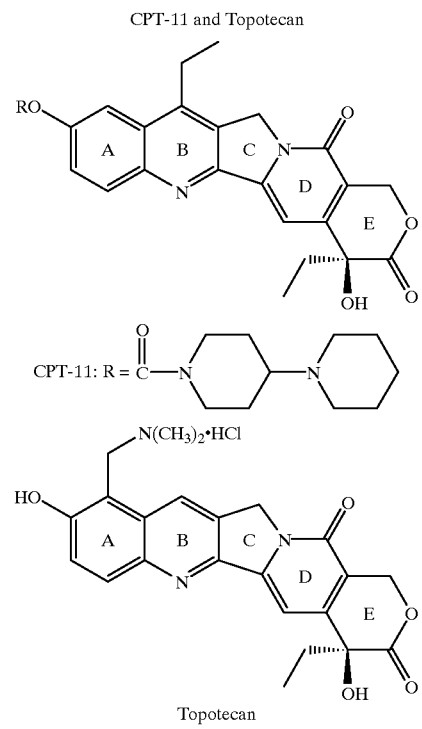

CPT-11 and Topotecan

Topotecan pH Mediated Hydrolysis of Camptothecin 20(S) Lactone E-ring

Lactone Form

Very Poorly Water Soluble
Potent Antitumor Activity

Carboxylate Form

Increased Water Solubility
Loss of Antitumor Activity

SUMMARY OF THE INVENTION

Accordingly, the inventors have pursued the development of novel, lactone stable pharmaceutical formulations for poorly water soluble and highly lipophilic camptothecins.

The instant invention is novel and useful because of the following:

(1) incorporation of lipophilic (soluble in organic media) chemical substitutions at the camptothecin skeleton 20(S) position, with or without additional structural modifications of the camptothecin skeleton, will result in greater lactone E ring stability in alkaline pH environments;

(2) this greater lactone E ring stability of such molecules will provide more useful antitumor activity; and (3) the lipophilic nature of such novel 20 (S) moieties can enhance tissue penetration and drug delivery of such novel compositions since cell membranes are largely comprised of lipids.

The novel camptothecins of this invention consist of C20 substituted analogues of camptothecin. The derivatives are of the following formula I:

(I)

wherein:

$R_1$, $R_2$, $R_3$ and $R_4$ are each individually hydrogen, —X—($C_0$–$C_6$ alkyl, $C_1$–$C_6$ alkenyl or $C_2$–$C_6$ alkynyl)—$SiR_{12}R_{13}R_{14}$, —($C_0$–$C_6$ alkyl, $C_1$–$C_6$ alkenyl, $C_2$–$C_6$ alkynyl, phenyl or benzyl)—$NR_9R_{10}$, or $OR_6$, wherein at least one of $R_1$, $R_2$, $R_3$ and $R_4$ is other than hydrogen;

$R_6$ is hydrogen, lower alkyl, or an oxygen protecting group;

$R_7$ is hydrogen, $C_1$–$C_6$ alkyl or ($C_0$–$C_6$ alkyl)—$SiR_{16}R_{17}R_{18}$;

$R_9$ and $R_{10}$ are each individually hydrogen, lower alkyl or a nitrogen protecting group;

$R_{11}$ is carbonyl, sulfonyl, thiocarbonyl, sulfoxo, or $C_1$–$C_{16}$ alkyl;

$R_{12}$, $R_{13}$, and $R_{14}$ are each individually hydrogen or $C_1$–$C_{10}$ alkyl;

$R_{15}$, $R_{16}$, $R_{17}$, and $R_{18}$ are each individually hydrogen, $C_1$–$C_{16}$ alkyl, $C_1$–$C_{16}$ alkenyl, $C_1$–$C_{16}$ alkynyl, aryl, heterocycle, amino, hydroxy, or substituted derivatives thereof; or a pharmaceutically acceptable salt thereof.

The compounds of this invention are useful as antineoplastic agents, and have demonstrated particularly potent activity, both in vitro and in vivo, against several different solid tumors, including but not limited to cancers of the colon, breast, pancreas, stomach, kidneys, liver, prostate, testis, lung, brain, malignant melanoma, and others.

The compounds are preferably formulated for administration to the patient. The formulations are designed for either oral or parenteral administration, and include one or more pharmaceutically acceptable solvents, excipients and/or diluents combined with the active compound.

Accordingly, it is an object of this invention to provide for novel derivatives of camptothecin.

Another object of this invention is to provide for camptothecin derivatives which are potent inhibitors of Topoisomerase I, and which possess antineoplastic properties.

Another object of this invention is to provide for novel formulations of camptothecin derivatives.

Another object of this invention is to provide for novel methods of treating antineoplastic diseases.

Other objects of this invention will become apparent upon a reading of the following description.

DESCRIPTION OF THE PREFERRED EMBODIMENTS

The preferred embodiments herein described are not intended to be exhaustive, nor to limit the invention to the precise forms disclosed. They are chosen and described to best illustrate the principles of the invention, and its application and practical use to best enable others skilled in the art to follow its teachings.

DEFINITIONS

"Scaffold" means the fixed part of the molecule of the general formula given.

"Fragments" or "Moieties" are the variable parts of the molecule, designated in the formula by variable symbols, such as $R_x$, X or other symbols. Fragments may consist of one or more of the following:

"$C_x$–$C_y$ alkyl" means a straight or branched-chain aliphatic hydrocarbon containing as few as x and as many as y carbon atoms. Examples include "$C_1$–$C_6$ alkyl" (also referred to as "lower alkyl"), which includes a straight or branched chain hydrocarbon with no more than 6 total carbon atoms, and $C_1$–$C_{16}$ alkyl, which includes a hydrocarbon with as few as one up to as many as sixteen total carbon atoms, and others;

"$C_x$–$C_y$ alkylidene" means a bridging moiety formed of as few as "x" and as many as "y" —$CH_2$— groups;

"$C_x$–$C_y$ alkenyl or alkynyl" means a straight or branched chain hydrocarbon with at least one double bond (alkenyl) or triple bond (alkynyl) between carbon atoms;

"$C_x$–$C_y$ alkoxy" means a straight or branched hydrocarbon chain with as few as x and as many as y carbon atoms, with the chain bonded to the scaffold through an oxygen atom;

"Alkoxycarbonyl" means an alkoxy moiety bonded to the scaffold through a carbonyl;

"Halogen" or "Halo" means chloro, fluoro, bromo or iodo;

"Acyl" means —C(O)—X, where X is hydrogen, $C_x$–$C_y$ alkyl, aryl, $C_x$–$C_y$ alkenyl, $C_x$–$C_y$ alkynyl, or aryl;

"Acyloxy" means —O—C(O)—X, where X is hydrogen, $C_x$–$C_y$ alkyl, or aryl;

"$C_x$–$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" means an aromatic ring or ring system consisting of one or more rings, preferably one to three rings, fused or unfused, with the ring atoms consisting entirely of carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Heterocycle" means a cyclic moiety of one or more rings, preferably one to three rings, fused or unfused, wherein at least one atom of one of the rings is a non-carbon atom. Preferred heteroatoms include oxygen, nitrogen, sulfur and phosphorous, or any combination of two or more of those atoms; and "Substituted" modifies any of the above fragments (moieties) by replacing any, some or all of the hydrogen atoms with a moiety (moieties) as identified in the specification.

"Protecting groups" are those moieties which are attached to a particular atom, usually nitrogen or oxygen, and which prevent reaction at that position of the scaffold under specified conditions. Protecting groups allow substitutions to be performed at other parts of the molecule, and are well-known to those skilled in the art.

Examples of the above moieties are as follows:

$C_1$–$C_6$ alkyl includes methyl, ethyl, propyl, isopropyl, butyl, isobutyl, sec-butyl, tert-butyl, pentyl, hexyl, amyl and the like;

$C_2$–$C_8$ alkenyl or alkynyl includes vinyl, propenyl, butenyl, acetylenyl, propynyl, and other like moieties with one or more double and/or triple bonds;

Alkoxy includes methoxy, ethoxy, propoxy, and the like;

Alkoxycarbonyl includes methoxycarbonyl, ethoxycarbonyl, and others;

Acyl includes formyl, acetyl, propionyl and others;

Acyloxy includes formoxy, acetoxy, propionoxy, and the like;

Cycloalkyl includes cyclopropyl, cyclobutyl, cyclohexyl, indanyl, dihydronaphthalenyl, cyclohexenyl, and the like;

Aryl includes phenyl, naphthyl and anthracenyl, as well as substituted variants wherein one of the hydrogen atoms bonded to the ring atom is substituted by a halogen atom, an alkyl group, or another moiety;

Arylalkyl includes benzyl, phenethyl, and the like;

Arylalkenyl and arylalkynyl includes phenyl vinyl, phenylpropenyl, phenylacetylenyl, phenylpropynyl and the like; and Heterocycle includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

Substitutions for hydrogen atoms to form substituted derivatives include halo, alkyl, nitro, amino (also N-substituted, and N,N di-substituted amino), sulfonyl, hydroxy, alkoxy, phenyl, phenoxy, benzyl, benzoxy, trihalomethyl.

Protecting groups include t-butyl-dimethyl silyl (TBDMS) and acetyl (oxygen), acetoxy (nitrogen), and the like.

The compounds of this invention are semisynthetic derivatives of camptothecin. In particular, the compounds are multi-substituted analogues derived from the camptothecin scaffold. All the derivatives are of the formula I, as depicted below (please note, that for purposes of this invention, the numbering scheme used to identify the CPT scaffold is as shown below, and the C20 chiral carbon is shown without the preferred S(−) stereochemistry).

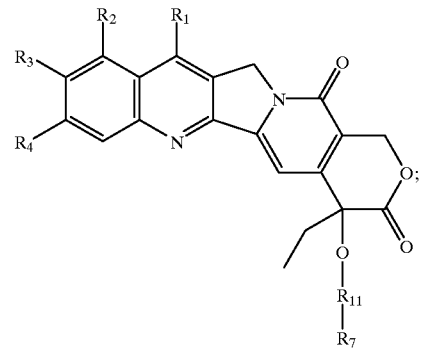

wherein:

$R_1$, $R_2$, $R_3$ and $R_4$ are each individually hydrogen, —X—($C_0$–$C_6$ alkyl, $C_1$–$C_6$ alkenyl or $C_2$–$C_6$ alkynyl)—$SiR_{12}R_{13}R_{14}$, —($C_0$–$C_6$ alkyl, $C_1$–$C_6$ alkenyl, $C_2$–$C_6$ alkynyl, phenyl or benzyl)—$NR_9R_{10}$, or $OR_6$, wherein at least one of $R_1$, $R_2$, $R_3$ and $R_4$ is other than hydrogen;

$R_6$ is hydrogen, lower alkyl, or an oxygen protecting group;

$R_7$ is hydrogen, $C_1$–$C_6$ alkyl or ($C_0$–$C_6$ alkyl)—$SiR_{16}R_{17}R_{18}$;

$R_9$ and $R_{10}$ are each individually hydrogen, lower alkyl or a nitrogen protecting group;

$R_{11}$ is carbonyl, sulfonyl, thiocarbonyl, sulfoxo, or $C_1$–$C_{16}$ alkyl;

$R_{12}$, $R_{13}$, and $R_{14}$ are each individually hydrogen or $C_1-C_{10}$ alkyl;

$R_{15}$, $R_{16}$, $R_{17}$, and $R_{18}$ are each individually hydrogen, $C_1-C_{16}$ alkyl, $C_1-C_{16}$ alkenyl, $C_1-C_{16}$ alkynyl, aryl, heterocycle, amino, hydroxy, or substituted derivatives thereof; or a pharmaceutically acceptable salt thereof.

The formula I compounds preferably include those compounds wherein $R_1$ is -(lower alkyl)—SiMe$_3$. Also in the preferred compounds, at least one of $R_2$ through $R_4$ is a moiety other than hydrogen, producing various di- and tri-substituted analogs of naturally occurring Camptothecin. Preferred $R_{11}$ moieties include most oxo moieties, such as carbonyl and sulfoxo, and also alkyls and alkylidenes, with preferred $R_7$ moieties including alkylsilyls.

Most preferred compounds include those compounds where $R_1$ is a -lower alkyl-silane moiety, one or two of $R_2$ through $R_4$ is amino, substituted amino, hydroxy, alkoxy, -carbonyl-lower alkyl-heterocycle, or aryloxy.

Most preferred compounds also include those where $R_{11}$ is carbonyl or sulfoxo or sulfonyl and $R_7$ is a trialkylsilyl moiety.

The 20-substituted analogues of the formula I compounds are synthesized according to the following scheme. The processes for effecting substitutions at the 7, 9, 10 and 11 positions of the 'A' and 'B' rings are set forth in detail in U.S. Pat. Ser. No. 5,910,491 and U.S. patent application Ser. Nos. 09/178,780 and 09/022,310, incorporated herein by reference.

Scheme 1

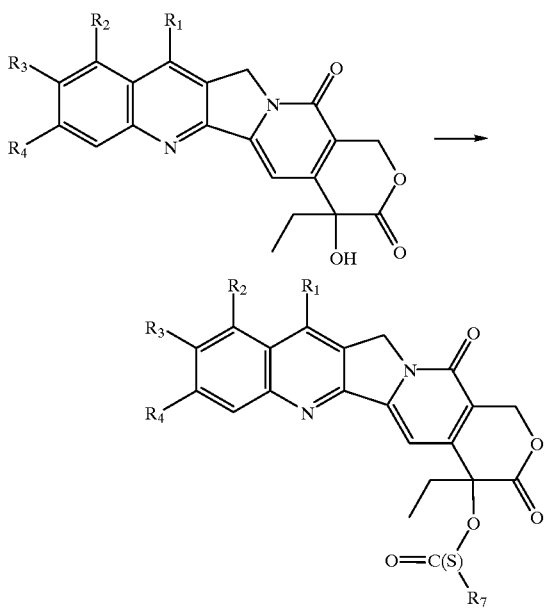

Scheme 1 illustrates the preferred process for derivatization of the C20 position of the camptothecin scaffold. In the preferred process, the moieties at C7, C9–C11 are attached prior to C20 derivatization, and protected if necessary by accepted and known means.

As shown, the preferred C20 derivatization involves a single step process, with the $R_{11}$ and $R_7$ variables dependent upon the reagents and conditions used in the derivatization. The preferred type of reagents include acids and acid chlorides, with the hydrogen atom of the 20-hydroxy moiety acting as a leaving group. When an acid is employed as a reactant, a basic solution is preferred to facilitate the substitution.

The specific examples which follow illustrate a preferred synthesis for two preferred compounds, with the understanding that other derivatives are synthesized through similar processes.

EXAMPLE 1

7-(β-trimethylsilyl)ethyl-20-acetoxy camptothecin 7-(β-trimethylsilyl)ethyl-20(S) camptothecin (100 mg) is dissolved in anhydrous methylene chloride and acetyl chloride (5 ml) added. The homogeneous solution is then stirred at room temperature until the complete consumption of 7-(β-trimethylsilyl)ethyl-20(S) camptothecin. The reaction mixture is then quenched using crushed ice and the product is extracted with methylene chloride (200 ml×3). The combined organic portion is then washed with water (50 ml), and dried over anhydrous sodium sulfate. The filtrate from the drying agent is then concentrated to obtain the desired product in its crude form. The crude product thus obtained is then column purified using flash chromatography eluting out the product using 90% hexane in ethyl acetate.

$^1$H NMR (300 MHz, CDCl$_3$): d 0.17 (9H, s); 0.93 (2H,m); 0.97 (3H, t, J=6.0 Hz); 2.219 (3H, s); 2.15–2.22 (2H, m); 3.13 (2H, m); 5.23 (2H, s); 5.37–5.71 (2H, ABq, J$_1$=19.2, J$_2$=66 Hz); 7.69 (1H,t, J=3 Hz); 7.82 (1H, t); 8.05 (1H, d, J=9.0); 8.25 (1H, 3H, J=9.0)

EXAMPLE 2

7-(β-trimethylsilyl)ethyl-20-(γ-trimethylsilyl-propionyl) camptothecin 7-(γ-trimethylsilyl)ethyl-20(S) camptothecin (100 mg, 0.22 mmol) is dissolved in anhydrous methylene chloride (10 ml) and 3-trimethylsilyl propionic acid (37.6 mg, 0.26 mmol) is added. To the above homogeneous solution is then added dicyclohexyl carbodiimide (DCC, ~0.1 ml) followed by 4-dimethylamino pyridine (DMAP, 33 mg, 0.26 mmol). The above reaction mixture is then stirred under a blanket of argon until the completion of reaction. The reaction mixture is then quenched using crushed ice and the product extracted with ethyl acetate (200 ml×3). The combined organic portion is then washed with water (50 ml), and dried over anhydrous sodium sulfate. The filtrate from the drying agent is then concentrated to obtain the desired product in its crude form. The crude product thus obtained is then column purified using flash chromatography eluting out the product using 90% hexane in ethyl acetate.

$^1$H NMR (300 MHz, CDCl$_3$): d 0.17 (9 H, s); 0.93 (2H, m); 0.95 (2 H, m); 0.97 (3H, t, J=6.0 Hz); 2.219 (3H, m); 2.15–2.22 (2H, m); 3.13 (2H, m); 5.23 (2H, s); 5.37–5.71 (2H, ABq, J$_1$=19.2, J$_2$=66 Hz); 7.69 (1H,t, J=3 Hz); 7.82 (1H, t); 8.05 (1H, d, J=9.0); 8.25 (1H, 3H, J=9.0).

The above descriptions are not intended as limiting of the invention, which may be modified along the scope of the following claims.

What is claimed is:

1. A compound having the formula:

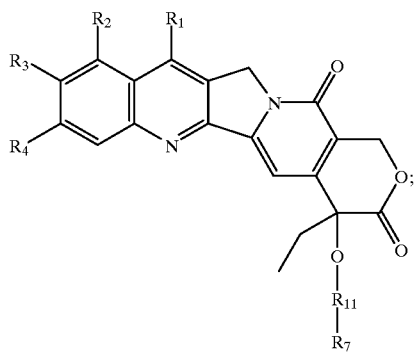

(I)

wherein:

$R_1$, $R_2$, $R_3$ and $R_4$ are each individually hydrogen; or —($C_0$–$C_6$ alkylene, $C_1$–$C_6$ alkenylene or $C_2$–$C_6$ alkynylene)—$SiR_{12}R_{13}R_{14}$, —($C_0$–$C_6$ alkylene, $C_1$–$C_6$ alkenylene, $C_2$–$C_6$ alkynylene, phenylene or benzylene)—$NR_9R_{10}$, or $OR_6$, wherein one or more hydrogen atoms of these moieties are optionally substituted by halo, lower alkyl, nitro, amino, substituted amino, hydroxy, lower alkoxy, aryloxy or trihalomethyl groups; wherein at least one of $R_1$, $R_2$, $R_3$ and $R_4$ is other than hydrogen;

$R_6$ is hydrogen, lower alkyl, or an oxygen-protecting group;

$R_7$ is —($C_0$–$C_6$ alkylene)—$SiR_{16}R_{17}R_{18}$;

$R_9$ and $R_{10}$ are each individually hydrogen, lower alkyl or a nitrogen-protecting group;

$R_{11}$ is carbonyl, sulfonyl, thiocarbonyl or sulfoxo;

$R_{12}$, $R_{13}$, and $R_{14}$ are each individually hydrogen or $C_1$–$C_{10}$ alkyl;

$R_{16}$, $R_{17}$, and $R_{18}$ are each individually hydrogen, $C_1$–$C_{16}$ alkyl, $C_1$–$C_{16}$ alkenyl, $C_1$–$C_{16}$ alkynyl, aryl,; or a pharmaceutically acceptable salt thereof.

2. The compound of claim 1 wherein one of $R_1$–$R_4$ is -lower alkyl-trimethylsilyl.

3. The compound of claim 1 wherein $R_7$ is -lower alkyl-trimethylsilyl.

4. The compound of claim 3 wherein $R_{11}$ is carbonyl.

5. The compound of any of claims 1, 2, 3 or 4 wherein two of $R_1$–$R_4$ are other than hydrogen.

6. The compound of claim 1 wherein three of $R_1$–$R_4$ are other than hydrogen.

7. A pharmaceutical formulation comprising the compound of claim 1, and one or more pharmaceutically acceptable excipients, fillers, or diluents.

8. A pharmaceutical formulation comprising the compound of claim 4, and one or more pharmaceutically acceptable excipients, fillers, or diluents.

9. A pharmaceutical formulation comprising the compound of claim 6, and one or more pharmaceutically acceptable excipients, fillers, or diluents.

10. The compound of claim 1 wherein $R_1$ is -ethyl-trimethylsilyl, $R_{11}$ is carbonyl, and $R_7$ is -ethyl-trimethylsilyl.

* * * * *